United States Patent [19]

Romano et al.

[11] 4,100,351

[45] Jul. 11, 1978

[54] METHOD FOR PREPARING AROMATIC URETHANS

[75] Inventors: Ugo Romano, Milan; Renato Tesei, San Donato Milanese (Milan), both of Italy

[73] Assignee: Anic, S.p.A., Palermo, Italy

[21] Appl. No.: 781,065

[22] Filed: Mar. 24, 1977

[30] Foreign Application Priority Data

Apr. 14, 1976 [IT] Italy ................. 22299 A/76

[51] Int. Cl.$^2$ ........................... C07C 125/06
[52] U.S. Cl. ........................ 560/24; 560/25; 560/27; 560/28
[58] Field of Search ............ 260/471 C; 560/24, 25, 560/27, 28

[56] References Cited

U.S. PATENT DOCUMENTS

| | | | |
|---|---|---|---|
| 3,763,217 | 10/1974 | Brill | 260/471 C |
| 3,819,683 | 6/1974 | Krebs et al. | 260/471 C |
| 3,938,986 | 2/1976 | Pray | 71/111 |
| 4,021,469 | 5/1977 | Weston | 260/471 C |

OTHER PUBLICATIONS

Illuminati et al., "Chem. Absts.", 105287m, vol. 84, 1976.

*Primary Examiner*—James O. Thomas, Jr.
*Assistant Examiner*—G. T. Breitenstein
*Attorney, Agent, or Firm*—Ralph M. Watson

[57] ABSTRACT

In the preparation of aromatic urethans, a dialkyl carbonate is reacted with an N-acyl derivative of an amine: thus, for example, by reacting acetanilide with a lower dialkyl carbonate, such as DMC or DEC, in the presence of titanium tetraphenate (Lewis' acid), phenyl-methyl urethan is obtained with a yield over 90%. No toxic reactants are used and the reaction has outstandingly high yields and conversion ratings. The urethane in question are useful as weed-killers and pesticides in agriculture.

6 Claims, No Drawings

METHOD FOR PREPARING AROMATIC URETHANS

This invention relates to a method for preparing aromatic urethans having the general formula:

and

in which Ar and Ar' are aromatic groups of the type phenyl, biphenyl, naphthyl and derivatives of diphenylmethane, possibly substituted by alkyl, alkoxy and aryl groups, R is an alkyl.

It is known that such compounds are synthesized starting from the respective amines and chloroformates, or from isocyanates and alcohols, by procedures which involve the use of highly toxic reactants.

It is likewise known that such a class of products finds an application in the field of weed-killers and pesticides.

It has recently been found that such compounds can be synthesized from amines and dialkylcarbonates in the presence of Lewis' acids (U.S. Pat. No. 3 763 217), but, in the reaction, along with the expected products, ureas and alkylamines are also obtained.

It has now been found that such compounds can be obtained with a virtually total selectivity and conversion if the dialkyl carbonate concerned is caused to react with an N-acyl derivative of the amine having the structure

and wherein Ac is a

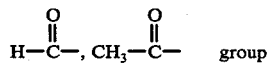 group and in general an acyl group deriving from a carboxylic organic, aliphatic or aromatic acid.

The reaction takes place in the presence of Lewis' acids and more particularly halides, alcoholates and phenates of aluminum and titanium.

During progress of the reaction, aromatic urethans and esters are formed. The reaction as such is carried out at a temperature ranging from 50° to 200° C and under a pressure comprised between 0.1 and 20 abs. atmospheres.

A few examples are reported by way of illustration and without any limitation.

EXAMPLE 1

In a 250-ml flask topped by a 20-plate column and a liquid-dividing head, 132 grams of diethylcarbonate (DEC), 25.1 grams of acetanilide and 4.8 grams of titanium tetraphenate have been reacted.

After 1 hour at 130° C there have been obtained 16 grams (yield 96%) of ethyl acetate as a head distillate.

The yield of phenylmethylurethan has been over 90%.

The conversion of acetanilide was 100%. No diphenylurea has been detected.

EXAMPLE 2

In the same apparatus as in Example 1 there have been charged 100.5 grams of dimethylcarbonate (DMC) and 25.1 grams of acetanilide with 4.8 grams of titanium tetraphenate.

After 2 hours at 110° C there have been obtained as a head distillate 13.3 grams of methyl acetate (yield 96.2%).

The yield of phenylmethylurethan was over 90%.

The conversion of acetanilide was 100%.

EXAMPLE 3

A 500-ml flask has been charged with 19.5 grams of N,N'-bis-acetyl-2,4-tolylene diamine and 300 grams of DMC with 2.4 grams of Ti(O Ph)$_4$.

After 5 hours at 120° C there have been obtained 13.9 grams of methyl acetate as the head distillate (yield 100%) and 22 grams of bis-methyl urethan of the tolylenediamine (yield 99%).

EXAMPLE 4

In the same apparatus as in Example 1 there have been charged 10 grams of acetanilide, 80 grams of DMC and 1.27 grams of Titanium tetramethylate.

After 4 hours at 120° C there have been distilled off as a head distillate 7.5 grams of methyl acetate (yield 72%) with a 80% conversion of acetanilide.

There have been obtained about 10 grams of phenylmethyl urethan with a yield of about 70% and a selectivity of 70%.

EXAMPLE 5

In the same apparatus as in Example 1 there have been charged 20 grams of acetanilide, 80 grams of DMC and 1.51 grams of Al(O-isopropyl)$_3$.

After 4 hours at 120° C there have been obtained as a head distillate 13.1 grams of methyl acetate and 18.4 grams of phenylmethyl urethan (yield 85%) with an acetanilide conversion of 90%.

EXAMPLE 6

The apparatus of Example 1 has been charged with 23 grams of propionanilide, 85 grams of DMC and 1.5 grams of TiCl$_4$.

After 4 hours a yield of 100% of methylpropionate as the head distillate has been obtained, with a total conversion of the propionanilide and a yield of 92% approx. of phenylmethylurethan.

We claim:

1. The method of preparing an aromatic urethan represented by the general formula:

or

wherein Ar and Ar' are aromatic groups deriving from phenyl, biphenyl, naphthyl, diphenylmethane, unsubstituted or substituted by alkyl, alkylalkoxy or aryl groups, and R is alkyl, which comprises reacting a dialkyl carbonate with an N-acyl derivative of an amine having the formula:

or

Ac—NH—Ar'—NH—Ac wherein Ar and Ar' have the significance given above and Ac is

or

R' being an alkyl or an aryl radical, in the presence of a Lewis acid selected from the group consisting of the halides, alcoholates and phenates of aluminum or titanium, in the temperature range of from 50° to 200° C and in the pressure range of from 0.1 to 20 abs. atmospheres.

2. The method of preparing an aromatic urethan as claimed in claim 1, wherein said dialkyl carbonate is diethyl carbonate and said amine is acetanilide.

3. The method of preparing an aromatic urethan as claimed in claim 1, wherein said dialkyl carbonate is dimethyl carbonate and said amine is acetanilide.

4. The method of preparing an aromatic urethan as claimed in claim 1, wherein said dialkyl carbonate is dimethyl carbonate and said amine is N, N'-bis-acetyl-2,4-tolylene diamine.

5. The method of preparing an aromatic urethan as claimed in claim 1, wherein said dialkyl carbonate is dimethyl carbonate and said amine is propionanilide.

6. The method of preparing an aromatic urethan as claimed in claim 1, wherein said Lewis acid is a member of the group consisting of titanium tetraphenate, titanium tetramethylate, titanium tetrachloride and Al(O-isopropyl)$_3$.

* * * * *